(12) United States Patent
Saito et al.

(10) Patent No.: US 7,772,577 B2
(45) Date of Patent: Aug. 10, 2010

(54) PARTICLE BEAM THERAPY SYSTEM

(75) Inventors: Kazuyoshi Saito, Hitachi (JP); Hiroaki Sakurabata, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 156 days.

(21) Appl. No.: 12/190,909

(22) Filed: Aug. 13, 2008

(65) Prior Publication Data

US 2009/0065706 A1  Mar. 12, 2009

(30) Foreign Application Priority Data

Aug. 17, 2007  (JP)  ............................. 2007-212704

(51) Int. Cl.
  *H05H 12/04*  (2006.01)
  *A61N 5/00*  (2006.01)
  *H01J 3/14*  (2006.01)

(52) U.S. Cl. .......... 250/505.1; 250/492.3; 250/396 ML; 315/503; 315/500; 315/111.61; 313/363.1

(58) Field of Classification Search .............. 250/505.1, 250/396 ML, 492.3; 315/503, 500, 111.61; 313/363.1
See application file for complete search history.

(56) References Cited

U.S. PATENT DOCUMENTS

| | | | |
|---|---|---|---|
| 5,363,008 A * | 11/1994 | Hiramoto et al. | ............. 313/62 |
| 7,102,144 B2 | 9/2006 | Matsuda et al. | |
| 7,122,978 B2 * | 10/2006 | Nakanishi et al. | ............ 315/500 |
| 2005/0231138 A1 | 10/2005 | Nakanishi et al. | |
| 2009/0114852 A1 * | 5/2009 | Saito et al. | ................ 250/492.3 |
| 2009/0309038 A1 * | 12/2009 | Balakin | ................... 250/396 R |

FOREIGN PATENT DOCUMENTS

| | | |
|---|---|---|
| EP | 0779081 | 6/1997 |
| EP | 1 477 206 | 11/2004 |
| JP | 2596292 | 1/1997 |
| JP | 2833602 | 10/1998 |
| JP | 2005/332794 | 12/2005 |

(Continued)

OTHER PUBLICATIONS

Takuji Furukawa et al., "Fast Beam Cut-Off Method in RF-Knockout Extraction for Spot-Scanning", Nuclear Instruments and Methods in Physics Research A489, Mar. 2002, pp. 59-67.

(Continued)

*Primary Examiner*—Nikita Wells
(74) *Attorney, Agent, or Firm*—Brundidge & Stanger, P.C.

(57) ABSTRACT

A particle beam therapy system using a spot scanning method includes a synchrotron, a beam transport system, an irradiation system, and a controller. A controller is configured to turn on a radio frequency electromagnetic field to be applied to an extraction system when a charged particle beam is to be supplied to the irradiation system, and turn off the radio frequency electromagnetic field to be applied to the extraction system when the supply of the charged particle beam to the irradiation system is to be blocked by means of an electromagnet provided in the beam transport system or in the synchrotron. The controller is also adapted to turn off a radio frequency acceleration voltage to be applied to an acceleration cavity in synchronization with the turning-off of the radio frequency electromagnetic field to be applied to the extraction device.

4 Claims, 6 Drawing Sheets

FOREIGN PATENT DOCUMENTS

JP          3874766         11/2006

OTHER PUBLICATIONS

Furukawa et al., "Characteristics of fast beam switching for spot scanning", Nuclear Instruments & Methods in Physics Research, Section—A: Accelerators, Spectrometers, Detectors and Associated Equipment, Elsevier, Amsterdam, Netherlands, vol. 503, No. 3, May 11, 2003, pp. 485-495, XP004426042.

Search Report in European Patent Application No. 08014394.4-1226/2026640 dated Feb. 3, 2010.

\* cited by examiner

PARTICLE BEAM THERAPY SYSTEM

BACKGROUND OF THE INVENTION

1. Field of the Invention

The present invention relates to a particle beam therapy system capable of high precision irradiation for treatment, and more particularly to a particle beam therapy system suitable for using a spot scanning irradiation method.

2. Description of the Related Art

In the recent aging society, a typical one of radiation therapies has attracted attention as one of cancer treatments since the radiation therapy is noninvasive to and has a low impact on human bodies. In addition, after the radiation therapy, the quality of life is highly maintained. Among the radiation therapies, a particle beam therapy system is a promising approach since the system provides an excellent dose concentration for an affected area of a patient. The particle beam therapy system uses a proton or a charged particle beam such as carbon, which is accelerated by an accelerator. The particle beam therapy system includes an accelerator, a beam transport system and an irradiation system (refer to Japanese Patent No. 2833602). The accelerator such as a synchrotron is adapted to accelerate a beam emitted by an ion source to a level close to the speed of light. The beam transport system is adapted to transport the beam extracted from the accelerator. The irradiation system is adapted to irradiate the beam on an affected area of a patient in conformity with the location and shape of the affected area.

Conventionally, in an irradiation system provided in a particle beam therapy system, a beam is formed by increasing the diameter of the beam by means of a scatterer and removing an outer periphery of the beam by means of a collimator in order to irradiate the beam on an affected area of a patient in conformity with the shape of the affected area. In this conventional method, the efficiency of using the beam is low, and an unnecessary neutron tends to be generated. In addition, there is a limitation in matching the shape of the beam with the shape of an affected area of a patient. Recently, the need of a scanning irradiation method has been increased as a higher precision irradiation method. In the scanning irradiation method, a beam having a small diameter is output from an accelerator, and bent by means of an electromagnet. An affected area of a patient is then scanned by means of the beam in conformity with on the shape of the affected area.

In the scanning irradiation method, a three-dimensional shape of an affected area is divided into a plurality of layers in a depth direction, and each of the layers is two-dimensionally divided into a plurality of portions. A plurality of irradiation spots is then set. Each of the layers is selectively irradiated with an irradiation beam by adjusting the energy of an irradiation beam dependent on the depth position of the layer. Each of the layers is two-dimensionally scanned with the irradiation beam by means of an electromagnet. The irradiation beam is irradiated on each irradiation spot with a predetermined dose. A method for continuously turning on an irradiation beam while the beam spot is moved from an irradiation spot to another irradiation spot is called raster scanning, whereas a method for turning off an irradiation beam while the beam spot is moved from an irradiation spot to another irradiation spot is called spot scanning. The spot scanning method is disclosed in Japanese Patent No. 3874766, for example.

In the conventional spot scanning method, a beam is irradiated on each irradiation spot with a predetermined dose under the condition that beam scanning is stopped. After the irradiation beam is turned off, the amount of an exciting current flowing in a scanning magnet is adjusted, and the beam spot is moved to the location of the next irradiation spot. To achieve high precision irradiation for treatment using the spot scanning method, it is necessary to position a spot of an irradiation beam with high accuracy and to turn on and off the irradiation beam at a high speed.

To obtain high accuracy of positioning of the irradiation beam spot, a known beam extraction method is used. In the beam extraction method, when a beam is extracted from a synchrotron, the size of the circulating beam is increased by means of a radio frequency (RF) power, and a particle having a large amplitude and exceeding a stability limit is extracted (refer to Japanese Patent No. 2596292). In this method, since an operation parameter of an extraction-related device for a synchrotron can be set to be constant during the extraction of the particle, orbit stability of the extracted beam is high. Therefore, an irradiation beam can be positioned with high accuracy, which is required for the spot scanning method.

However, it takes a certain time to block the extracted beam even when radio frequency (RF) power for extraction is turned off at the time of termination of irradiation on each spot. Thus, irradiation (delayed irradiation) occurs during the delay time. The delayed irradiation dose is not allowable in the spot scanning method in general. The beam extracted from the synchrotron is controlled to prevent the beam from reaching an irradiation system by turning on and off a shielding magnet provided in a beam transport system during movement of the beam spot from an irradiation spot to another irradiation spot. It is known that an irradiation beam is blocked by turning on and off a quadrupole magnet provided in a synchrotron at a high speed during movement of a beam spot from an irradiation spot to another irradiation spot (refer to JP-A-2005-332794).

Non-patent Document 1, "Fast beam cut-off method in RF-knockout extraction for spot-scanning", Nuclear Instruments and Methods in Physics Research A489 (2002) 59-67 discloses an operation for turning off a radio frequency acceleration voltage to be applied to the synchrotron in synchronization with the turning-off of the extraction RF power as a method for reducing a delayed irradiation dose of a beam irradiated immediately after the termination of the irradiation on each spot in the case where the beam extraction method described in Japanese Patent No. 2596292 is used. In this method, the delayed irradiation dose of the beam irradiated immediately after the turning-off can be reduced. However, after the turning-off, the extracted beam with a small irradiation dose may leak in an area present between irradiation spots. Especially, the extracted beam with a relatively large irradiation dose may leak in an area present between irradiation spots during the change in the amount of the exciting current flowing in the scanning magnet in a remote spot irradiation method in which the irradiation spots are remotely located and are to be irradiated. In addition, the radio frequency acceleration voltage is turned off for a long time during movement of a beam spot from an irradiation spot to another irradiation spot in the remote spot irradiation method. The beam circulating in the synchrotron therefore becomes unstable. This results in a reduction in the quality of the irradiation beam.

SUMMARY OF THE INVENTION

In each of the methods described in Japanese Patent No. 2596292 and JP-A-2005-332794, a power supply and an electromagnet, which are adapted to turn on and off the extracted beam, are necessary. As a result, a system using any one of the methods described in Japanese Patent No. 2596292 and JP-A-2005-332794 is expensive.

In a method described in Non-Patent Document 1, a delayed irradiation dose of a beam irradiated immediately after the turning-off can be reduced. However, after that, the extracted beam with a small irradiation dose may leak in an area present between irradiation spots. Especially, the extracted beam with a relatively large irradiation dose may leak in an area present between irradiation spots during the change in the amount of the exciting current flowing in the scanning magnet in the remote spot irradiation method in which the irradiation spots are remotely located and are to be irradiated. In addition, the radio frequency acceleration voltage is turned off for a long time during movement of a beam spot from an irradiation spot to another irradiation spot in the remote spot irradiation method. The beam circulating in the synchrotron therefore becomes unstable. This results in a reduction in the quality of the irradiation beam.

It is a first object of the present invention to provide a particle beam therapy system capable of achieving an irradiation beam suitable for a particle beam therapy using a spot scanning method. The particle beam therapy system can be realized at low cost.

It is a second object of the present invention to provide a particle beam therapy system capable of providing a therapy for a remote irradiation spot with an improved irradiation beam in a remote spot irradiation method in which an irradiation spot is remotely located and is to be irradiated. The particle beam therapy system can be realized at low cost and is capable of achieving an irradiation beam suitable for a particle beam therapy using a spot scanning method.

(1) To accomplish the first object, a particle beam therapy system comprises: a synchrotron for accelerating a charged particle beam by means of a radio frequency acceleration voltage applied to an acceleration cavity such that the charged particle beam has a predetermined energy level, causing the charged particle beam to exceed a stability limit by means of a radio frequency electromagnetic field applied to an extraction device, and then extracting the thus-prepared charged particle beam; a beam transport system for introducing the charged particle beam extracted from said synchrotron to a treatment room; an irradiation system for irradiating an affected area of a patient with the charged particle beam in conformity with the shape of the affected area in the treatment room; and a controller for turning on the radio frequency electromagnetic field to be applied to the extraction device when the charged particle beam is to be supplied to said irradiation system, turning off the radio frequency electromagnetic field to be applied to the extraction device when the supply of the charged particle beam to said irradiation system is to be blocked by means of an electromagnet provided in said beam transport system or in said synchrotron, and turning off the radio frequency acceleration voltage to be applied to the acceleration cavity in synchronization with the turning-off of the radio frequency electromagnetic field to be applied to the extraction device.

The particle beam therapy system constructed as described above is capable of achieving an irradiation beam suitable for a particle beam therapy using a spot scanning method and can be realized at low cost.

(2) For the particle beam therapy system described in the abovementioned (1), it is preferable that the electromagnet, which is adapted to block the supply of the charged particle beam to the irradiation system and is provided in the beam transport system, be a bending magnet for producing a dipole magnetic field.

(3) For the particle beam therapy system in the abovementioned (1), it is preferable that the electromagnet, which is adapted to block the supply of the charged particle beam to the irradiation system and is provided in the synchrotron, be a focusing magnet or a defocusing magnet, which produces a quadrupole magnetic field.

(4) To accomplish the second object, a particle beam therapy system comprises: a synchrotron for accelerating a charged particle beam by means of a radio frequency acceleration voltage applied to an acceleration cavity such that the charged particle beam has a predetermined energy level, causing the charged particle beam to exceed a stability limit by means of a radio frequency electromagnetic field applied to an extraction device, and then extracting the thus-prepared charged particle beam; a beam transport system for introducing the charged particle beam extracted from said synchrotron to a treatment room; an irradiation system for irradiating an affected area of a patient with the charged particle beam in conformity with the shape of the affected area in the treatment room; and a controller used for turning on the radio frequency electromagnetic field to be applied to the extraction device when the charged particle beam is to be supplied to said irradiation system, turning off the radio frequency electromagnetic field to be applied to the extraction device when the supply of the charged particle beam to said irradiation system is to be blocked by means of an electromagnet provided in said beam transport system or in said synchrotron, turning off the radio frequency acceleration voltage to be applied to the acceleration cavity in synchronization with the turning-off of the radio frequency electromagnetic field to be applied to the extraction device, and turning on the radio frequency acceleration voltage to be applied to the acceleration cavity at least once under the condition which the radio frequency electromagnetic field to be applied to the extraction device is turned off.

The particle beam therapy system constructed as described above is capable of providing a therapy for a remote irradiation spot with an improved irradiation beam in a remote spot irradiation method in which an irradiation spot is remotely located and is to be irradiated. The particle beam therapy system can be realized at low cost and is capable of achieving an irradiation beam suitable for a particle beam therapy using a spot scanning method.

According to the present invention, the particle beam therapy system is capable of achieving an irradiation beam suitable for a particle beam therapy using a spot scanning method and can be realized at low cost.

In addition, according to the present invention, the particle beam therapy system is capable of providing a therapy for a remote irradiation spot with an improved irradiation beam in a remote spot irradiation method in which an irradiation spot is remotely located and is to be irradiated. The particle beam therapy system can be realized at low cost and is capable of achieving an irradiation beam suitable for a particle beam therapy using a spot scanning method.

DESCRIPTION OF THE PREFERRED EMBODIMENTS

A description will be made of the configuration and operations of a particle beam therapy system according to a first embodiment of the present invention with reference to FIGS. 1 to 5F.

First, a description will be made of the entire configuration of the particle beam therapy system according to the first embodiment and the principle of irradiation of a particle beam with reference to FIGS. 1 to 3B.

Figure 1:
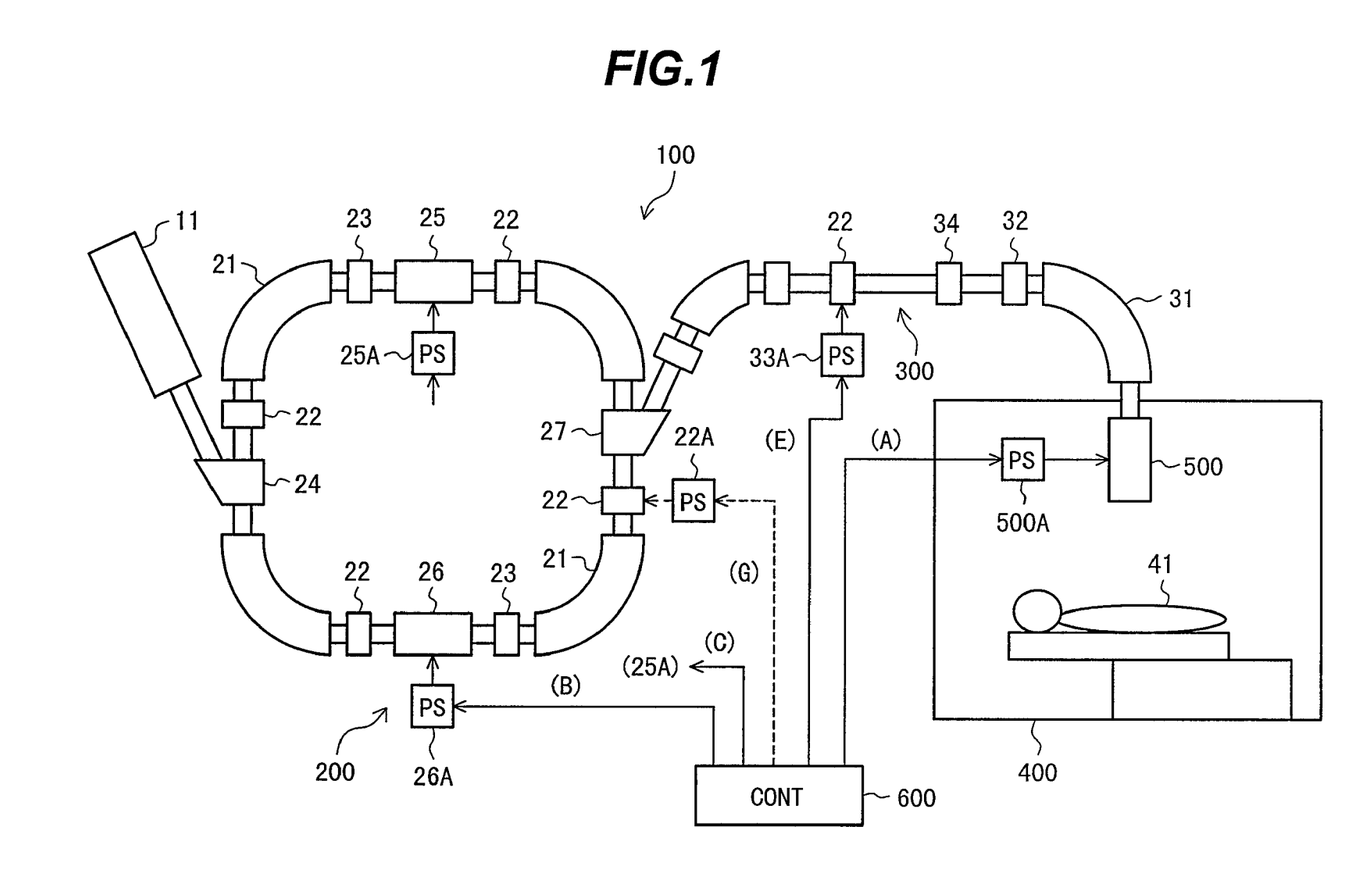
FIG. 1 is a diagram showing the configuration of a particle beam therapy system according to a first embodiment of the present invention.

FIG. 1 is a diagram showing the configuration of the particle beam therapy system according to the first embodiment.

In FIG. 1, reference numeral 100 denotes the particle beam therapy system. The particle beam therapy system 100 includes a synchrotron 200, a beam transport system 300, an irradiation system 500 and a controller 600. The synchrotron 200 is adapted to accelerate a charged particle beam (pre-accelerated by a pre-accelerator 11 such as a linac) in order that the charged particle beam has a predetermined energy level and adapted to output the charged particle beam. The beam transport system 300 is adapted to introduce the charged particle beam extracted from the synchrotron 200 to a treatment room 400. The irradiation system 500 is adapted to irradiate the charged particle beam on an affected area of a patient 41 in conformity with the shape of the affected area.

The synchrotron 200 includes a beam injection device 24, a bending magnet 21, a quadrupole magnet 22, a power supply 22A, an acceleration cavity 25, a power supply 25A, sextupole magnets 23, an extraction device 26, a power supply 26A and an extraction bending device 27. The beam injection device 24 is adapted to receive a charged particle beam pre-accelerated by the pre-accelerator 11. The bending magnet 21 is adapted to bend the charged particle beam in order to cause the charged particle beam to circulate on a constant orbit. The quadrupole magnet 22 is adapted to apply focusing forces directed in horizontal and vertical directions to the charged particle beam to prevent the charged particle beam from spreading. The power supply 22A is provided for the quadrupole magnet 22. The acceleration cavity 25 is adapted to accelerate the charged particle beam by means of a radio frequency acceleration voltage in order that the charged particle beam has a predetermined energy level. The power supply 25A is adapted to supply a radio frequency acceleration voltage to the acceleration cavity 25. The sextupole magnet 23 is adapted to form a stability limit for an oscillation amplitude of the circulating charged particle beam. The extraction device 26 is adapted to increase the oscillation amplitude of the charged particle beam by means of a radio frequency electromagnetic field in order to ensure that the charged particle beam exceeds the stability limit and adapted to extract the charged particle beam from the synchrotron 200. The power supply 26A is adapted to supply radio frequency (RF) power for extraction to the extraction device 26. The extraction bending device 27 is adapted to bend the charged particle beam in order to output the charged particle beam from the synchrotron 200.

A description will be made of a method for extracting a charged particle beam from the synchrotron provided in the particle beam therapy system according to the first embodiment with reference to FIGS. 2A and 2B.

Figure 2A:
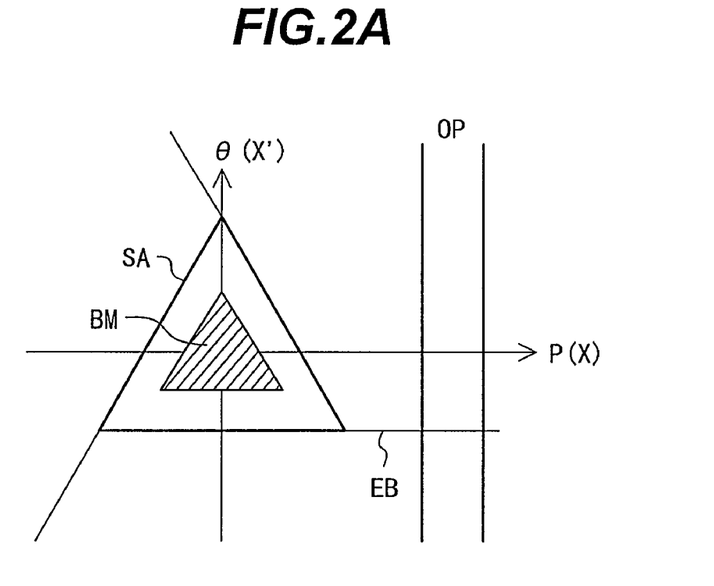
FIGS. 2A and 2B are explanatory diagrams each showing a method for extracting a charged particle beam from a synchrotron in the particle beam therapy system according to the first embodiment.
Figure 2B:
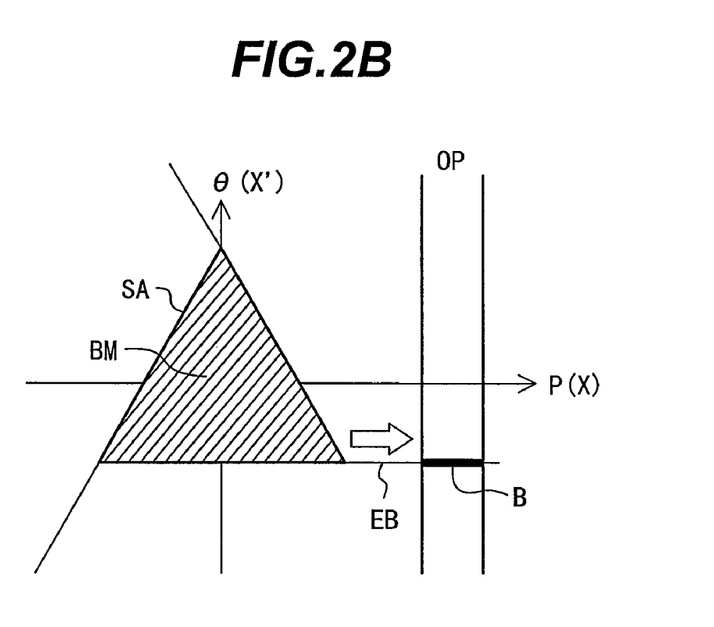

FIGS. 2A and 2B are explanatory diagrams each showing a method for extracting a charged particle beam from the synchrotron provided in the particle beam therapy system according to the first embodiment.

Each of FIGS. 2A and 2B shows the state of the charged particle beam circulating in the synchrotron within a phase space in the horizontal direction, which is related to the extraction. In each of FIGS. 2A and 2B, an abscissa axis indicates the position (P) of the charged particle beam shifted from a design orbit, and an ordinate axis indicates an inclination (angle θ) with respect to the design orbit. FIG. 2A shows the phase space in the horizontal direction before the start of the extraction. FIG. 2B shows the phase space in the horizontal direction after the start of the extraction.

As shown in FIG. 2A, each of particles constituting the charged particle beam oscillates around the design orbit in the horizontal direction/the vertical direction. The charged particle beam circulates as a circulating beam BM. A triangle-shaped stable region SA is formed in the phase space by exciting the sextupole magnet 23 shown in FIG. 1. A particle present in the stable region SA continues to stably circulate in the synchrotron.

In this case, when radio frequency power for extraction is applied to the extraction device 26 shown in FIG. 1, the amplitude of the circulating beam BM is increased as shown in FIG. 2B. An oscillation amplitude of a particle output from the stable region SA is rapidly increased along an extraction branch EB. The particle output from the stable region SA finally enters an opening portion OP of the extraction bending device 27 and is extracted from the synchrotron as an extracted beam B.

The size of the stable region is determined based on the amount of an exciting current flowing in the quadrupole magnet 22 or the sextupole magnet 23. FIG. 2A shows the phase space before the start of the extraction. FIG. 2B shows the phase space after the start of the extraction. The size of the stable region SA is set to be larger than emittance (which is an extent occupied by particles of the charged particle beam in the phase space) of the charged particle beam before the start of the extraction. To extract the charged particle beam from the synchrotron, a radio frequency electromagnetic field for the extraction is applied to the extraction device 26. The emittance of the charged particle beam then becomes large (the oscillation amplitudes of particles are increased), and a particle exceeding the stability limit is extracted from the synchrotron. The extracted beam can be controlled to be turned on and off by turning on and off the radio frequency electromagnetic field for the extraction. The amount of the exciting current flowing in the magnet is constant during the extraction. The stable region and the extraction branch are not varied during the extraction. The position and the size of the spot of the extracted beam are therefore stable. An irradiation beam suitable for the scanning method can be achieved.

Referring back to FIG. 1, the beam transport system 300 includes a bending magnet 31, a focusing/defocusing quadrupole magnet 32, a beam shielding magnet 33, a power supply 33A and a beam dump 34. The bending magnet 31 is adapted to bend the charged particle beam extracted from the synchrotron by means of a magnetic field and introduce the beam to the treatment room 400 along a predetermined design orbit. The focusing/defocusing quadrupole magnet 32 is adapted to apply focusing forces directed in the horizontal and vertical directions to the charged particle beam to prevent the charged particle beam from spreading during the transport of the charged particle beam. The beam shielding magnet 33 is adapted to turn on and off the supply of the charged particle beam to the irradiation system 500 provided in the treatment room 400. The power supply 33A is provided for the beam shielding magnet 33. The beam dump 34 is adapted to discard a beam component removed by the beam shielding magnet 33.

It should be noted that the beam shielding magnet 33 may bend an unnecessary beam component by means of a dipole magnetic field generated during excitation to discard the unnecessary beam component by the beam dump 34 or may bend a beam component by means of the dipole magnetic field generated during the excitation to supply only the beam component to the irradiation system 500. In the former method, the beam transport system can be easily adjusted. In the latter method, since the supply of the charged particle beam to the irradiation system is blocked under the condition that a device is abnormal, the system is highly secure.

Figure 3A:
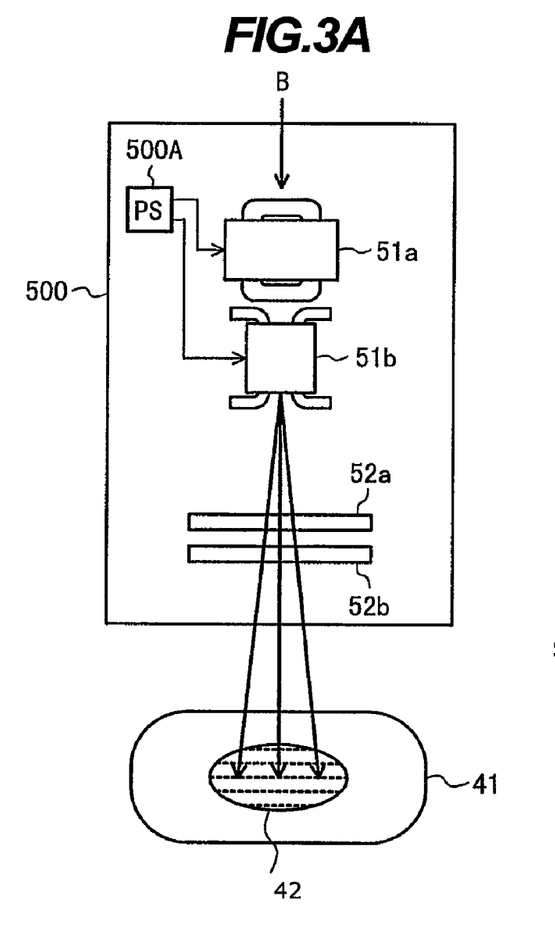
FIG. 3A is a front view of an irradiation system provided in the particle beam therapy system according to the first embodiment.

The irradiation system 500 has a power supply 500A provided for scanning magnets 51a and 51b shown in FIG. 3A.

Figure 3B:
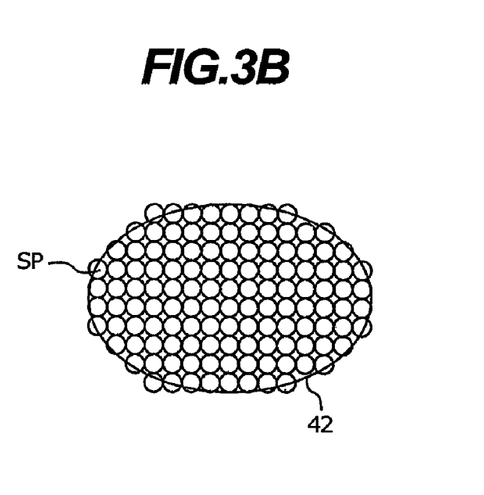
FIG. 3B is an explanatory diagram showing irradiation beams when viewed from the top.
Figure 4:
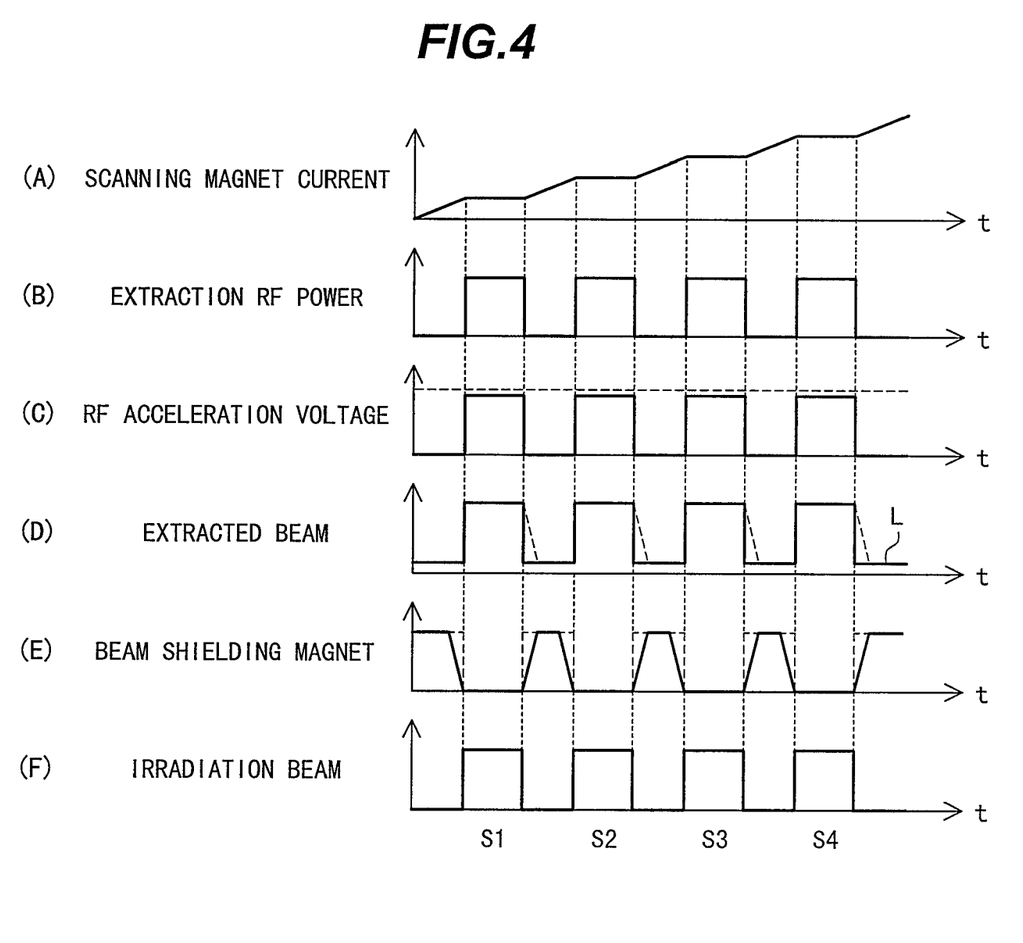
FIGS. 4A to 4F are timing charts showing operations in a first example of a spot scanning method used in the particle beam therapy system according to the first embodiment.
Figure 5:
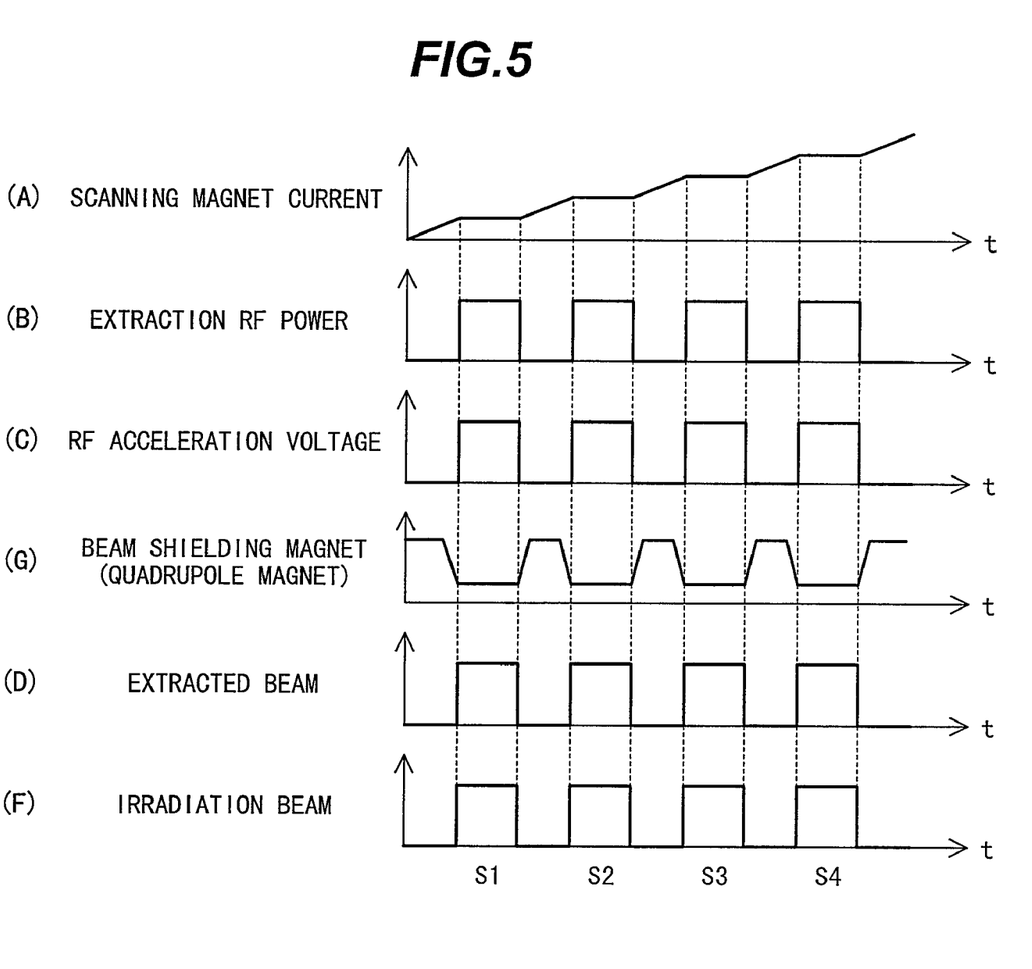
FIGS. 5A to 5F are timing charts showing operations in a second example of the spot scanning method used in the particle beam therapy system according to the first embodiment.
Figure 6:
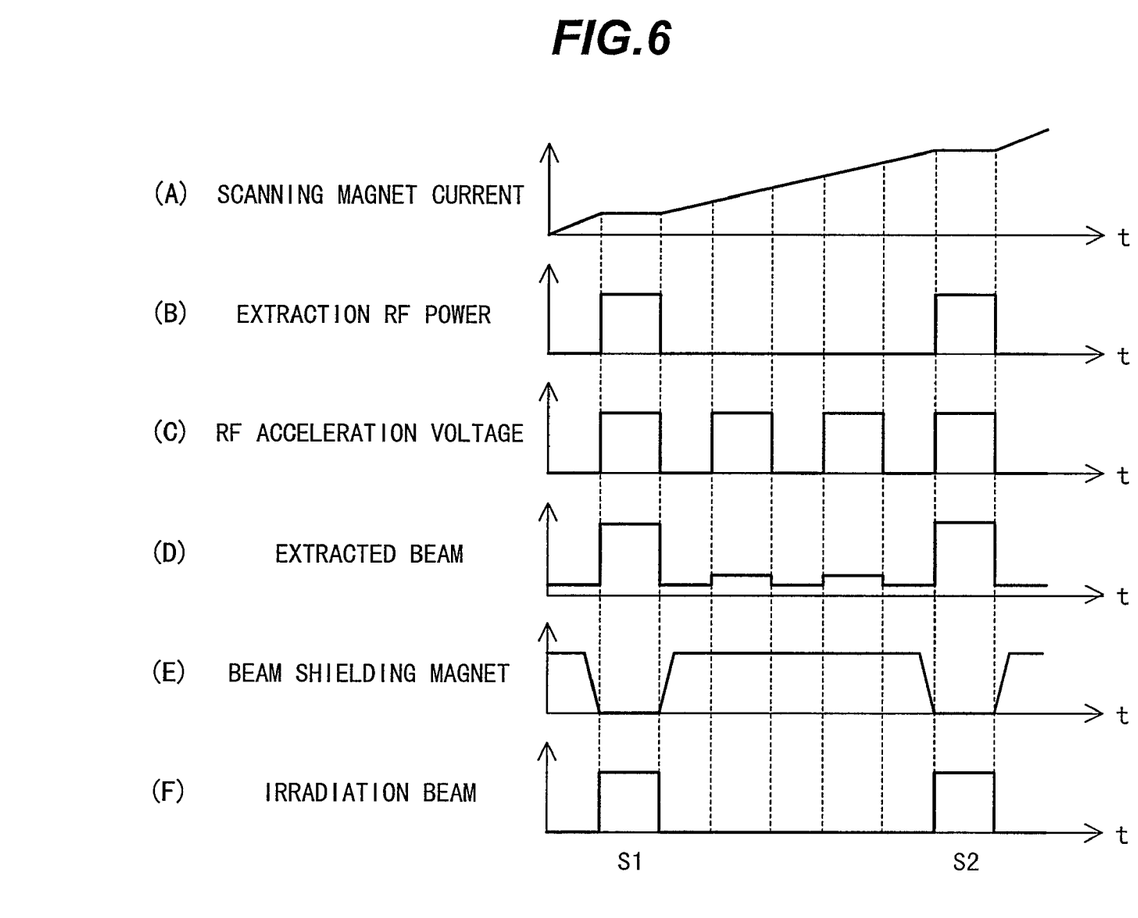
FIGS. 6A to 6F are timing charts showing operations of a spot scanning method in which a remote spot irradiation method can be performed in a particle beam therapy system according to a second embodiment of the present invention.

A description will be made of the configuration of the irradiation system 500 used in the particle beam therapy system according to the present invention with reference to FIGS. 3A and 3B.

FIG. 3A is a front view of an irradiation system provided in the particle beam therapy system according to the first embodiment.

The irradiation system 500 includes the scanning magnets 51a and 51b, the power supply 500A and beam monitors 52a and 52b. The scanning magnets 51a and 51b are adapted to bend the charged particle beam introduced by the beam transport system 300 to the horizontal and vertical directions in order to two-dimensionally scan an affected area 42 of a patient 41 in conformity with the cross sectional shape of the affected area 42. The power supply 500A is provided for the scanning magnets 51a and 51b. The beam monitors 52a and 52b are adapted to monitor the position, size and dose of the charged particle beam.

The spot scanning method will be described with reference to FIGS. 3A and 3B. FIG. 3B is an explanatory diagram showing irradiation beams when viewed from the top (when viewed from B direction shown in FIG. 3A).

As shown in FIG. 3A, the affected area 42 of the patient 41 is divided into a plurality of layers in a three-dimensional depth direction. Each of the layers is divided into a plurality of portions two-dimensionally to set a plurality of irradiation spots. Each of the layers located at depth positions different from each other is selectively irradiated with the irradiation beam by adjusting the energy level of the beam extracted from the synchrotron and thereby changing the energy level of the irradiation beam. As shown in FIG. 3B, the scanning magnet 51a or 51b (collectively referred to as the scanning magnet 51) bends the irradiation beam for scanning in order that the irradiation beam is irradiated on respective irradiation spots SP present on each of the layers with respective predetermined doses. In this case, when the predetermined dose of the irradiation beam is provided to one of the irradiation spots SPs, the irradiation beam is blocked at a high speed. After the shielding, the beam spot is moved to the location of another irradiation spot under the condition that the irradiation beam is turned off. The irradiation is progressed in this way to perform the spot scanning.

Next, a description will be made of operations in a first example of the spot scanning method used in the particle beam therapy system according to the present embodiment.

FIGS. 4A to 4F are timing charts showing operations in the first example of the spot scanning method used in the particle beam therapy system according to the present embodiment.

In FIGS. 4A to 4F, each of abscissa axes indicates a time t. An ordinate axis of the timing chart shown in FIG. 4A indicates the amount of a current supplied to the scanning magnet 51 from the power supply 500A in response to a scanning command signal supplied to the power supply 500A from the controller 600. An ordinate axis of the timing chart shown in FIG. 4B indicates the extraction RF power supplied to the extraction device 26 from the power supply 26A in response to an extraction RF control signal supplied to the power supply 26A from the controller 600. An ordinate axis of the timing chart shown in FIG. 4C indicates a radio frequency acceleration voltage supplied to the acceleration cavity 25 from the power supply 25A in response to a RF acceleration voltage control signal supplied to the power supply 25A from the controller 600. An ordinate axis of the timing chart shown in FIG. 4D indicates the on and off states of a beam extracted from the synchrotron 200 to the beam transport system 300. An ordinate axis of the timing chart shown in FIG. 4E indicates the on and off states of the beam shielding magnet 33 in response to a beam shielding control signal supplied to the power supply 33A from the controller 600. An ordinate axis of the timing chart shown in FIG. 4F indicates the on and off states of the irradiation beam irradiated from the irradiation system 500. When the irradiation beam is in the on state, spots S1, S2, S3 and S4 are formed.

In FIGS. 4C to 4E, dashed lines indicate operations performed in a conventional spot scanning method.

As shown in FIG. 4A, an area to be irradiated with the irradiation beam is scanned by increasing a current to be supplied to the scanning magnet 51 from the power supply 500A, and an area to be irradiated with the irradiation beam is specified by maintaining a current to be supplied to the scanning magnet 51 from the power supply 500A. In the spot scanning method, the irradiation beam is irradiated on each of the irradiation spots S1, S2 and S3 with a predetermined dose under the condition that the beam scanning is stopped, and after the irradiation beam is turned off, the amount of the exciting current flowing in the scanning magnet is adjusted in order that the irradiation beam is moved to the location of the next irradiation spot, as shown in FIGS. 4A to 4F.

As shown in FIG. 4B, the radio frequency electromagnetic field is applied to the extraction device at the time of the spot irradiation in which the charged particle beam is supplied to the irradiation system, while the radio frequency electromagnetic field to be applied to the extraction device is turned off during the movement of the irradiation spot in which the supply of the charged particle beam to the irradiation system is blocked. At the same time, the supply of the charged particle beam is blocked by means of the beam shielding magnet provided in the beam transport system when the supply of the charged particle beam to the irradiation system is blocked, as shown in FIG. 4E.

Referring to FIG. 4C, the dashed line indicates a radio frequency acceleration voltage used in a conventional technique. The radio frequency acceleration voltage (indicated by the dashed line) supplied to the acceleration cavity 25 from the power supply 25A is constant. In the conventional technique, even when RF power for extraction is turned off as shown in FIG. 4B, it takes a certain time to block an extracted beam. Therefore, leakage L occurs due to the delay of the blocking as indicated by the dashed line shown in FIG. 4D. To avoid the leakage, the beam extracted from the synchrotron is controlled to prevent the beam from reaching the irradiation system by turning on the beam shielding magnet provided in the beam transport system at a high speed as indicated by a dashed line shown in FIG. 4E during the adjustment of the exciting current flowing in the scanning magnet for irradiation on the next irradiation spot. To increase or reduce an electromagnetic field generated by the beam shielding magnet and turn on or off the electromagnetic field at a high speed as indicated by the dashed line shown in FIG. 4E, an expensive electromagnet and an expensive power supply are necessary.

According to the present invention, the radio frequency acceleration voltage is turned off when the supply of the charged particle beam to the irradiation system is to be blocked as indicated by a solid line shown in FIG. 4C. Specifically, the radio frequency acceleration voltage to be applied to the acceleration cavity is turned off in synchronization with the turning-off of the radio frequency electromagnetic field to be applied to the extraction device. This suppresses energy oscillation of the charged particle beam circulating in the synchrotron. Therefore, an irradiation dose of a delayed charged particle beam, which exceeds the stability limit and is extracted from the synchrotron immediately after the blocking due to the energy oscillation, can be reduced. This can reduce an irradiation dose of the extracted beam (which is, for example, a charged particle beam that circulates in the synchrotron, collides with a residual gas, exceeds the stability limit, and is extracted from the synchrotron) leaking in an area present between irradiation spots even when a power supply, which is provided for the beam shielding magnet and is turned on and off at a low speed, is used. An electromagnet, which is turned on and off at a low speed, is much more inexpensive than an electromagnet, which is turned on and off at a high speed.

Accordingly, an irradiation beam suitable for the spot scanning method can be achieved at low cost.

Next, a description will be made of operations in a second example of the spot scanning method used in the particle beam therapy system according to the present embodiment with reference to FIGS. 5A to 5F.

FIGS. 5A to 5F are timing charts showing operations in the second example of the spot scanning method used in the particle beam therapy system according to the present embodiment.

In FIGS. 5A to 5F, each of abscissa axes indicates a time t. Ordinate axes of the timing charts shown in FIGS. 5A to 5F are the same as those of the timing charts shown in FIGS. 4A to 4F, respectively. In the timing chart shown in FIG. 5F, the quadrupole magnet 22 shown in FIG. 1 is used as the beam shielding magnet. The ordinate axis of the timing chart shown in FIG. 5F indicates the on and off states of the quadrupole magnet 22 in response to a beam shielding control signal supplied to the power supply 22A from the controller 600.

In the example shown in FIGS. 4A to 4F, the bending magnet for producing a dipole magnetic field is provided in the beam transport system and used as the beam shielding magnet. However, the focusing/defocusing quadrupole magnet 22, which produces a quadrupole magnetic field and is provided in the synchrotron, may be used.

As described above, the stability limit is varied based on the amount of the exciting current flowing in the quadrupole magnet 22 provided in the synchrotron. When the supply of the charged particle beam to the irradiation system is to be blocked, the stability limit is increased by means of the quadrupole magnet 22, the extraction of the charged particle beam is blocked as shown in FIG. 5F, and the radio frequency acceleration voltage to be applied to the acceleration cavity is turned off as shown in FIG. 5C.

In this case, it is not necessary that the quadrupole magnet (used as the beam shielding magnet) and an excitation power supply for the quadrupole magnet be operated at a high speed. Therefore, an irradiation beam suitable for the spot scanning method can be achieved at low cost. Both the bending magnet provided in the beam transport system and the quadrupole magnet provided in the synchrotron may be used as the beam shielding magnet to improve reliability of the particle beam therapy system.

As shown in FIG. 1, the number of the quadrupole magnets 22 provided in the synchrotron 100 is four. In the example shown in FIG. 1, the power supply 22A provided for one of the quadrupole magnets 22 is controlled by the controller 600. The four quadrupole magnets 22 may be controlled simultaneously.

According to the present embodiment, it is not necessary that the electromagnet and the power supply, which are adapted to turn on and off the beam extracted from the synchrotron, be operated at a high speed. This can reduce the cost of the particle beam therapy system.

Next, a description will be made of the configuration and operations of a particle beam therapy system according to a second embodiment of the present invention with reference to FIGS. 1 to 6F. In the second embodiment, a spot scanning method in which remote spot irradiation can be performed is used. It should be noted that the entire configuration of the particle beam therapy system according to the second embodiment is the same as that of the particle beam therapy system shown in FIG. 1.

FIGS. 6A to 6F are timing charts showing operations of the particle beam therapy system according to the second embodiment in the spot scanning method in which the remote spot irradiation can be performed.

In FIGS. 6A to 6F, each of abscissa axes indicates a time t. Ordinate axes of the timing charts shown in FIGS. 6A to 6F are the same as those of the timing charts shown in FIGS. 4A to 4F, respectively.

Similarly to the example shown in FIGS. 4A to 4F, the radio frequency electromagnetic field is applied to the extraction device at the time of the spot irradiation in which the charged particle beam is supplied to the irradiation system, while the radio frequency electromagnetic field to be applied to the extraction device is turned off during the movement of the irradiation spot in which the supply of the charged particle beam to the irradiation system is blocked, as shown in FIG. 6B. In order to block the supply of the charged particle beam to the irradiation system, the supply of the charged particle beam is blocked by means of the beam shielding magnet provided in the beam transport system as shown in FIG. 6E. As shown in FIG. 6C, after the radio frequency acceleration voltage to be applied to the acceleration cavity is turned off once, the radio frequency acceleration voltage is repeatedly turned on and off during the movement of the irradiation spot. When the time period for turning on the radio frequency acceleration voltage shown in FIG. 6B is defined as T1, it is preferable that the radio frequency acceleration voltage be repeatedly turned on for the time period of T1 and turned off for the time period of T1 during the off state of the radio frequency electromagnetic field for extraction. Even when the radio frequency acceleration voltage is turned on and off only once, an effect of stabilizing the circulating beam occurs.

Specifically, the radio frequency acceleration voltage to be applied to the acceleration cavity is turned off in synchronization with the turning-off of the radio frequency electromagnetic field to be applied to the extraction device. This suppresses energy oscillation of the charged particle beam circulating in the synchrotron. Therefore, an irradiation dose of a delayed charged particle beam, which exceeds the stability limit and is extracted from the synchrotron immediately after the blocking due to the energy oscillation, can be reduced. This can reduce an irradiation dose of the extracted beam (which is, for example, a charged particle beam that circulates in the synchrotron, collides with a residual gas, exceeds the stability limit, and is extracted from the synchrotron) leaking in an area present between irradiation spots even when a power supply, which is provided for the beam shielding magnet and is turned on and off at a low speed, is used.

In addition, the circulating beam can be stabilized by turning on the radio frequency acceleration voltage to be applied to the acceleration cavity at least once under the condition that the radio frequency electromagnetic field to be applied to the extraction device is turned off.

An irradiation dose of the beam (which is a problem with the remote spot irradiation) leaking in an area present between irradiation spots can be suppressed by turning on the excitation power supply provided for the beam shielding magnet as shown in FIG. 6E. A reduction in the quality of the irradiation beam due to instability of the beam circulating in the synchrotron during the remote spot irradiation can be avoided by repeatedly turning on and off the radio frequency acceleration voltage during the blocking of the supply of the beam and by increasing momentum spread of the beam with compensation for an energy loss of the circulating beam. The quality of the irradiation beam can be improved by repeatedly turning on and off the radio frequency acceleration voltage during the blocking of the supply of the beam.

Therefore, the irradiation beam can be stabilized and unnecessary administration of irradiation dose can be avoided even during the remote spot irradiation in which the remotely located irradiation spot is to be irradiated. As a result, a treatment using the remote spot irradiation for a complex affected area can be performed with high precision.

In the present embodiment, the bending magnet for producing a dipole magnetic field is provided in the beam transport system as the beam shielding magnet. The focusing/defocusing quadrupole magnet, which produces a quadrupole magnetic field and is provided in the synchrotron, may be used as the beam shielding magnet, as explained in the example of FIGS. 5A to 5F. Both the bending magnet provided in the beam transport system and the quadrupole magnet provided in the synchrotron may be used as the beam shielding magnet to improve the reliability of the particle beam therapy system.

According to the present embodiment, it is not necessary that the electromagnet and the power supply, which are adapted to turn on and off the beam extracted from the synchrotron, be operated at a high speed. This can reduce the cost of the particle beam therapy system.

In addition, the irradiation beam can be stabilized and unnecessary administration of irradiation dose can be avoided even during the remote spot irradiation in which a remotely located irradiation spot is to be irradiated. Therefore, a treatment using the remote spot irradiation for a complex affected area can be performed with high precision.

The present invention can be applied not only to a particle beam therapy system for a cancer treatment and the like but also to physics study requiring irradiation on a target with a high-energy charged particle beam accelerated by a synchrotron with high precision and a predetermined intensity distribution.

What is claimed is:

1. A particle beam therapy system comprising:
a synchrotron for accelerating a charged particle beam by means of a radio frequency acceleration voltage applied to an acceleration cavity such that the charged particle beam has a predetermined energy level, causing the charged particle beam to exceed a stability limit by means of a radio frequency electromagnetic field applied to an extraction device, and then extracting the thus-prepared charged particle beam;
a beam transport system for introducing the charged particle beam extracted from said synchrotron to a treatment room;
an irradiation system for irradiating an affected area of a patient with the charged particle beam in conformity with the shape of the affected area in the treatment room; and
a controller for turning on the radio frequency electromagnetic field to be applied to the extraction device when the charged particle beam is to be supplied to said irradiation system, turning off the radio frequency electromagnetic field to be applied to the extraction device when the supply of the charged particle beam to said irradiation system is to be blocked by means of an electromagnet provided in said beam transport system or in said synchrotron, and turning off the radio frequency acceleration voltage to be applied to the acceleration cavity in synchronization with the turning-off of the radio frequency electromagnetic field to be applied to the extraction device.

2. The particle beam therapy system according to claim 1, wherein
the electromagnet, which is provided in said beam transport system and adapted to block the supply of the charged particle beam to said irradiation system, is a bending magnet for producing a dipole magnetic field.

3. The particle beam therapy system according to claim 1, wherein
the electromagnet, which is provided in said synchrotron and adapted to block the supply of the charged particle beam to said irradiation system, is a focusing magnet for producing a quadrupole magnetic field or is a defocusing magnet for producing a quadrupole magnetic field.

4. A particle beam therapy system comprising:
a synchrotron for accelerating a charged particle beam by means of a radio frequency acceleration voltage applied to an acceleration cavity such that the charged particle beam has a predetermined energy level, causing the charged particle beam to exceed a stability limit by means of a radio frequency electromagnetic field applied to an extraction device, and then extracting the thus-prepared charged particle beam;
a beam transport system for introducing the charged particle beam extracted from said synchrotron to a treatment room;
an irradiation system for irradiating an affected area of a patient with the charged particle beam in conformity with the shape of the affected area in the treatment room; and
a controller for turning on the radio frequency electromagnetic field to be applied to the extraction device when the charged particle beam is to be supplied to said irradiation system, turning off the radio frequency electromagnetic field to be applied to the extraction device when the supply of the charged particle beam to said irradiation system is to be blocked by means of an electromagnet provided in said beam transport system or in said synchrotron, turning off the radio frequency acceleration voltage to be applied to the acceleration cavity in synchronization with the turning-off of the radio frequency electromagnetic field to be applied to the extraction device, and turning on the radio frequency acceleration voltage to be applied to the acceleration cavity at least once under the condition which the radio frequency electromagnetic field to be applied to the extraction device is turned off.

* * * * *